United States Patent

Oda et al.

Patent Number: 5,864,041
Date of Patent: Jan. 26, 1999

[54] PROCESS FOR PRODUCING THREO-3-(3,4-DIHYDROXYPHENYL)SERINE

[75] Inventors: Yoshiaki Oda, Toyonaka; Kazunori Iwakura, Takatsuki, both of Japan

[73] Assignee: Sumitomo Chemical Company, Ltd., Osaka, Japan

[21] Appl. No.: 899,635

[22] Filed: Jul. 24, 1997

Related U.S. Application Data

[62] Division of Ser. No. 650,539, May 20, 1996, Pat. No. 5,739,387.

[30] Foreign Application Priority Data

May 18, 1995 [JP] Japan .................................. 7-119864
May 18, 1995 [JP] Japan .................................. 7-119865

[51] Int. Cl.⁶ .................................................. C07D 263/52
[52] U.S. Cl. ........................................... 548/216; 548/215
[58] Field of Search ..................................... 548/216, 215

[56] References Cited

PUBLICATIONS

Shimamoto, K. & Ohfune, Y., *A New Entry to the Synthesis of β–Hydroxytyrosines Via a Novel Benzylic Hydroxylation*, Tetrahedron Letters, vol. 29, No. 40, pp. 5177–5180, 1988.
Hayashi, T. & Sawamura, M. & Ito, Y., *Asymmetric Synthesis Catalyzed by Chiral Ferrocenylphosphine–Transition Metal Complexes. $10^1$ Gold(I)–Catalyzed Asymmetric Aldol Reaction of Isocyanoacetate*, Tetrahedron, vol. 48, No. 11, pp. 1999–2012, 1992.
Chemical Abstracts 120:218452 & RN 154051–93–1, see abstract and compound in enclosed printout.
Chemical Abstracts 117:204212 & RNs 144125–91–7 & 144125–89–3, see abstract and compounds in enclosed printout.
Chemical Abstracts 113:132732 & RNs 129077–94–7 & 117831–96–6, see abstract and compound in enclosed printout.

*Primary Examiner*—Paul J. Killos
*Attorney, Agent, or Firm*—Cushman Darby Cushman IP Group of Pillsbury Madison & Sustro, LLP

[57] ABSTRACT

Racemic or optically active threo-3-(3,4-dihydroxyphenyl) serine can be readily produced via a few short steps by a process involving the steps of reacting a racemic or optically active N-acyl DOPA derivative represented by the formula [I]:

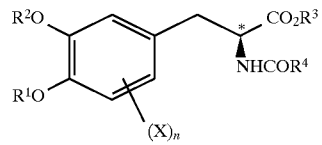

wherein X is a halogen atom; n is 0, 1, 2 or 3; $R^1$ and $R^2$ independently represent a protecting group for a hydroxyl group; $R^3$ is a protecting group for carboxyl group; $R^4$ is an alkyl group which may have a substituent or a phenyl group which may have a substituent; and a carbon marked with the symbol * is an asymmetric carbon, with a halogen radical generator, a cerium (IV) salt, or a persulfate salt in the presence of a copper catalyst to produce racemic or optically active oxazolines represented by the formula [IV]:

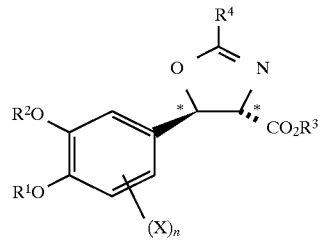

wherein $R^1, R^2, R^3, R^4$, X, n and * are as defined above; and thereafter conducting an oxazoline ring opening and removing $R^1, R^2$ and $R^3$ and, optionally, removing X when n is 1, 2 or 3.

2 Claims, No Drawings

PROCESS FOR PRODUCING THREO-3-(3,4-DIHYDROXYPHENYL)SERINE

This is a division of application Ser. No. 08/650,539, filed May 20, 1996, now U.S. Pat. No. 5,739,387.

BACKGROUND OF THE INVENTION

1. Field of the Invention

The present invention relates to a process for producing threo-3-(3,4-dihydroxyphenyl)serine.

2. Description of the Related Art

Threo-3-(3,4-dihydroxyphenyl)serine [III] (hereinafter described as threo DOPS) is pharmacologically active towards the circulatory system and the central nervous system, and, when administered to a patient, has efficacy against certain ailments, such as peripheral orthostatic hypotension and Parkinson disease, among others, and has efficacy as an antidepressant. This compound has been produced, for example, by using a derivative M of N-butoxycarbonyl DOPA obtained from N-acyl-3,4-dihydroxyphenylalanine (hereinafter referred to as DOPA) via three or four steps as described in Japanese Patent Kokai (Laid-Open) No. 1-228946.

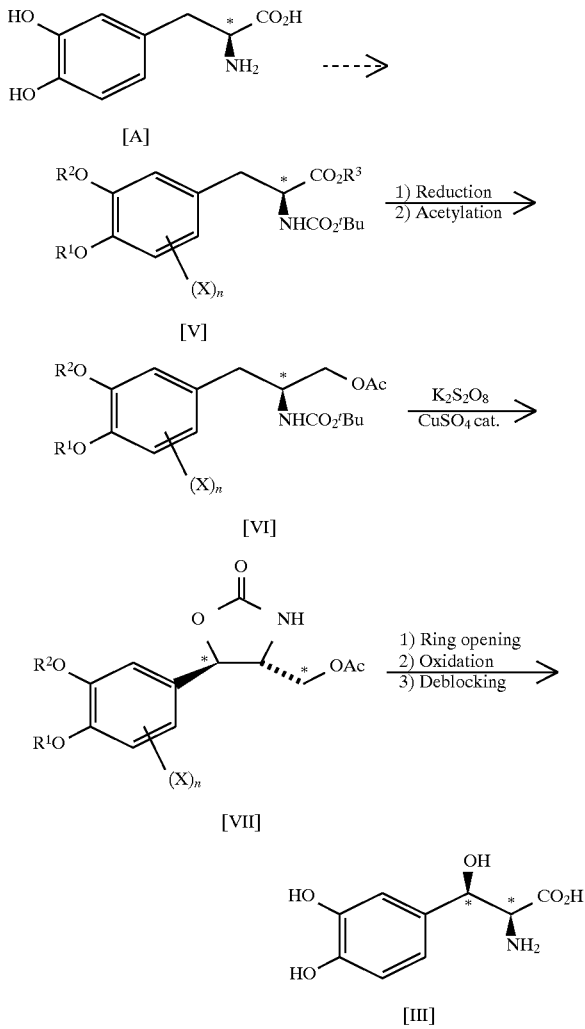

In this multi-step process, the oxazolidone intermediate having an acetoxymethyl group at the 4-position, compound [VII], is produced via following three reaction steps:

(1) reducing an alkoxycarbonyl moiety of the derivative [V] of N-butoxycarbonyl DOPA to form an alcohol;

(2) acetylating the alcohol to obtain an acetoxy-form [VI]; and (3) reacting the acetoxy-form [VI] with potassium persulfate in the presence of a copper catalyst to obtain the oxazolidone [VII] intermediate.

Thereafter, at least three further reaction steps are required before obtaining the desired threo-DOPS [III]:

(4) the oxazolidone ring is opened;

(5) the alcohol moiety derived from an acetoxy group is oxidized and converted into a carboxyl group; and then (6) protecting groups and halogen(s) are removed to obtain threo DOPS [III] as a final product.

Disadvantageously, however, this process requires at least six steps. This six-step operation is complicated and the yield of the final product, based on DOPA [A] as the starting material, is low.

It would be a significant advance to provide a more synthetically facile process for making threo DOPS [III].

A synthetically facile process which produces the desired threo DOPS [III] in higher yields with good selectivity would be particularly advantageous.

Such a process which is capable of being industrially practiced is particularly desirable.

Those skilled in the art have been seeking such processes.

SUMMARY OF THE INVENTION

Through intensive research, we have discovered a more facile process for the synthesis of racemic or optically active oxazolines [IV] in one stage by reacting a racemic or optically active N-acyl DOPA derivative [I] obtained from DOPA [A] in three or four steps with a halogen radical generator, a cerium (IV) salt in the presence or absence of a copper catalyst, or a persulfate salt in the presence of a copper catalyst.

We have also discovered that racemic or optically active threo DOPS [III] can be efficiently produced from the N-acyl DOPA derivative [I] in only two or three stages by the opening of the oxazoline ring of this oxazoline, elimination of the protecting group and, if necessary, elimination of halogen.

We have also discovered a facile process suitable for industrial practice which has an improved yield and good selectivity to the desired threo DOPS.

Our present invention therefore provides an excellent industrial scale process for producing racemic or optically active threo DOPS represented by the formula [III]:

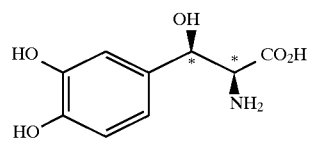

wherein * is as defined below, which comprises the steps of reacting racemic or optically active an N-acyl DOPA derivative represented by the formula [I]:

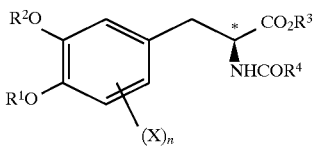

wherein X is a halogen atom; n is 0, 1, 2, or 3; $R^1$ and $R^2$ independently represent a protecting group for a hydroxyl group; $R^3$ is a protecting group for a carboxyl group; $R^4$ is an alkyl group which may have a substituent or a phenyl group which may have a substituent, a carbon marked with the symbol * is an asymmetric carbon, with a halogen, radical generator, a cerium (IV) salt in the presence or absence of a copper catalyst, or a persulfate salt in the presence of a copper catalyst to produce racemic or optically active oxazoline represented by the formula [IV]:

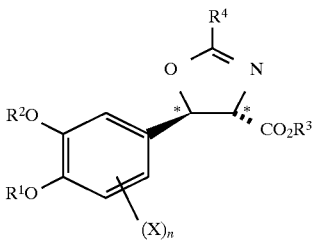

wherein $R^1$, $R^2$, $R^3$, $R^4$, X n and * are as defined above; and thereafter opening the oxazoline ring of said oxazoline and removing the $R^1$, $R^2$ and $R^3$ protecting groups and, further, removing X when n is 1, 2 or 3.

Our invention also provides a novel oxazoline and an N-acyl-3,4-dihydroxyphenylalanine derivative, which are useful as intermediates in the above synthesis of the pharmacologically effective threo DOPS.

DETAILED DESCRIPTION OF THE INVENTION

Preparation of Oxazoline [IV] from N-acyl DOPA Derivative [I]

The N-acyl DOPA derivative [I] which is a starting substance in the process of the present invention, is producible as described, hereinbelow. In the N-acyl DOPA derivation [I], $R^1$ and $R^2$ are the same or different and represent a protecting group for a hydroxyl group such as, for example, an alkyl group having 1 to 6 carbon atoms, (such as methyl, ethyl, n-propyl, isopropyl, butyl, sec-butyl, t-butyl, pentyl, hexyl, or cyclohexyl), an aralkyl group having 7 to 11 carbon atoms (such as benzyl, naphthylmethyl, or phenethyl) or an allyl group. $R^1$ and $R^2$ together may represent a methylene group which may be substituted with an alkyl group having 1 to 3 carbon atoms (methyl, ethyl, n-propyl, iso-propyl), an alkylene group having 4 or 5 carbon atoms (such as tetramethylene, pentamethylene) or an aryl group having 6 to 10 carbon atoms (such as phenyl, tolyl, or naphthyl). In these latter instances, $R^1$ and $R^2$ represent, for instance, 2-propylidene, 2-butylene, cyclohexylidene, benzylidene, and naphthylmethylene. Aralkyl, allyl and substituted-methylene hydroxy-protecting groups are preferred because they are easily eliminated.

$R^3$ represents a protecting group for a carboxyl group. Suitable $R^3$ carboxyl-protecting groups include, for example, a lower alkyl group having 1 to 6 carbon atoms such as methyl, ethyl, n-propyl, isopropyl, n-butyl, sec-butyl, t-butyl, pentyl, hexyl, and cyclohexyl; an aralkyl group having 7 to 11 carbon atoms such as benzyl, naphthylmethyl, or phenethyl; an allyl group; and an aryl group having 6 to 10 carbon atoms such as phenyl, tolyl, or naphthyl.

$R^4$ represents an optionally substituted alkyl group or an optionally substituted phenyl group. Suitable $R^4$ groups include, for instance, a lower alkyl group having 1 to 6 carbon atoms such as methyl, ethyl, n-propyl, isopropyl, n-butyl, tert-butyl, sec-butyl, pentyl, hexyl, and cyclohexyl; a lower alkyl halide group such as chloromethyl, dichloromethyl, trichloromethyl, fluoromethyl, or trifluoromethyl; a lower alkoxylated lower alkyl group such as methoxymethyl, methoxyethoxymethyl, or methoxypropyl; a lower alkoxylated phenyl group such as o-, m-, p-methoxyphenyl; a phenyl halide group such as o-, m-, p-chlorophenol, or o-, m-, p-bromophenol; a lower alkylated phenyl group such as o-, m-, p-tolyl; and a nitro-aryl group such as o-, m-, p-nitrophenyl group. As is used herein "lower alkyl" means having about 1 to about 6 carbon atoms.

X represents a halogen atom such as for example, chlorine, bromine, or iodine. When n is 1, 2 or 3, e.g., when the N-acyl DOPA derivative [I] is a halogen-substituted derivative, oxazolines [IV] can be obtained in higher yield.

Among the N-acyl DOPA derivatives [I], a compound wherein n is 1, 2 or 3 and $R^1$ and $R^2$ independently represent an alkyl group, aralkyl group or an allyl group, or $R^1$ and $R^2$ together can represent an optionally substituted methylene group, or when n is 0 and $R^1$ and $R^2$ independently represent an aralkyl group or an allyl group or $R^1$ and $R^2$ together can represent an optionally substituted methylene group is a novel and useful intermediate in the synthesis of pharmaceutically effective compounds such as threo DOPS [III]. N-acyl DOPA derivatives wherein $R^1$ and $R^2$ represent aralkyl, allyl and substituted-methylene groups are preferred because $R^1$ and $R^2$ are easily eliminated. When n is 1, 2 or 3, oxazolines [IV] can be obtained in higher yield.

Suitable exemplars of the N-acyl DOPA derivative [I] include, racemic and optically active N-acyl DOPA derivatives such as, for instance, methyl 2-acetylamino-3-(3,4-dimethoxyphenyl)propanoate, ethyl 2-acetylamino-3-(3,4-dibenzyloxyphenyl) propanoate, phenyl 2-acetylamino-3-(3,4-diallyloxyphenyl)propanoate, benzyl 2-benzoylamino-3-(3,4-dibenzyloxyphenyl)propanoate, benzyl 2-benzoylamino-3-(2-chloro-4,5-dimethoxyphenyl) propanoate, methyl 2-benzoylamino-3-(3,4-dibenzyloxyphenyl)propanoate, allyl 2-dichloroacetylamino-3-(3,4-methylenedioxy phenyl) propanoate, isopropyl 3-(3,4-isoropylidene dioxyphenyl)-2-(4-methoxy phenylamino) propanate, benzyl benzyl 2-benzoylamino(2-chloro-4,5-dibenzyloxyphenyl) propanoate, benzyl 2-benzoylamino-3-( 2-bromo4,5-dibenzyloxyphenyl)propanoate, methyl 2-benzoylamino-3-(2-bromo-4,5dimethioxyphenyl)propanoate, among others.

As used herein, alternative expressions for eliminating a protecting group, or elimination of a protecting group, include "removal" of the protecting group. This is also known as "de-blocking" or "de-protecting."

Reaction Conditions

The racemic or optically active oxazolines represented by the formula [IV]:

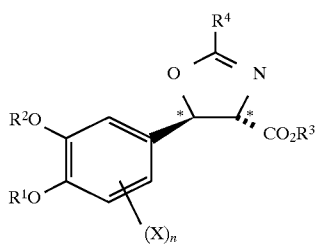

wherein $R^1$, $R^2$, $R^3$, X, N and * are as defined above, and can be obtained by reacting the N-acyl DOPA derivative [I] obtained by the process described below with the halogen radical generator, cerium (IV) salt in the presence or absence of a copper catalyst, or a persulfate in the presence of the copper catalyst. The optically active oxazolines represented by the formula [IV] are extremely important intermediates for producing racemic or optically active threo DOPS [III].

The oxazolines [IV] can be produced by reacting the N-acyl DOPA derivative [I] with the halogen radical generator. Suitable halogen radical generators, include, for example, N-halosuccinimides such as N-bromosuccinimide and N-chlorosuccinimide, molecular bromine, molecular chlorine, 1,3-dibromo-5,5-dimethylhydantoin, 5-bromo-2,2-dimethyl-1,3dioxane4,6-dione, and mixtures thereof. The halogen radical generator is normally used in an amount of about 1 to about 10 mol, preferably about 1 to about 2 mol, based on 1 mol of the N-acyl DOPA derivative [I]. In order to accelerate generation of halogen radical, a free radical forming agent can, if desired, be used in combination with the halogen radical generator. A free-radical generator as used herein includes free radical forming agents which can decompose to form free radicals. Suitable free radical forming agents include, for instance, organic azo compounds such as azobisisobutyronitrite, 2,2'-azobis (2, 4-dimethylvaleronitrile, 2,2'-azobis (4-methory-2, 4-dimethylvaleronitrile, and organic peroxides, such as benzoyl peroxide, m-chloroperbenzoic acid, and tert-butyl hydroperoxide. When used, the free radical forming agent is generally used in an amount of about 0.0001 to about 10 mol, preferably about 0.001 to about 1 mol, based on 1 mol of the N-acyl DOPA derivative [I].

The oxazolines [IV] also can be produced by reacting the N-acyl DOPA derivative [I] with a cerium (IV) salt. Inorganic cerium (IV) salts are preferred. Suitable inorganic cerium (IV) salts include, for example, ammonium cerium (IV) nitrate, cerium (IV) hydroxide, cerium (IV) sulfate, ammonium cerium (IV) sulfate, and mixtures thereof. The cerium (IV) salt is normally used in an amount of about 1 to about 6 mol, preferably about 2 to about 5 mol, based on 1 mol of the N-acyl DOPA derivative [I]. A copper catalyst can, if desired, be used in combination with the cerium (IV) salt. When used, this combination makes the reaction proceed more efficiently. Suitable copper catalysts include, for example, copper (I) chloride, copper (II) chloride, copper acetate, copper sulfate, and copper (II) hydroxide among others. The copper catalyst is normally used in an amount of about 0.01 to about 100% by mol, preferably about 0.1 to about 50% by mol, based on the N-acyl DOPA derivative [I].

The oxazolines [IV] can also be produced by reacting the N-acyl DOPA derivative [I] with a persulfate salt in the presence of a copper catalyst. Suitable persulfate salts include, for example, alkali or ammonium persulfates, such as sodium persulfate, potassium persulfate, ammonium persulfate, and mixtures thereof. The persulfate salt is normally used in an amount of about 1 to about 6 mol, preferably about 2 to about 5 mol, based on 1 mol of the N-acyl DOPA derivative [1]. Suitable copper catalysts are as described above, and therefore include, for example, copper (I) chloride, copper (II) chloride, copper acetate, copper sulfate, and copper (II) hydroxide, among others. The copper catalyst is normally used in an amount of about 0.01 to about 100% by mol, preferably about 0.1 to about 50% by mol, based on the N-acyl DOPA derivative [1].

The reaction for producing oxazolines from the N-acyl DOPA derivative [IV] is normally conducted in the presence of one or more solvents. Suitable solvents are inactive to the reaction and include, for example, hydrocarbon halides such as dichloromethane, chloroform, carbon tetrachloride, and monochlorobenzene; ketones such as lower alkyl ketones including acetone, methyl ethyl ketone; esters including lower alkyl esters of acetic acid such as ethyl acetate, and butyl acetate; nitriles such as acetonitrile, and propionitrile; ethers such as diethyl ether, methyl tert-butyl ether, tetrahydrofuran, and dioxane; organic acids including a lower alkyl carboxylic acids such as acetic acid, and propanoic acid; water; carbon disulfide; or a mixture of any thereof. The solvent is normally used in an amount of about 1- to about 100-fold by weight, preferably about 1- to about 10-fold by weight, based on the N-acyl DOPA derivative [I].

When using the halogen radial generator, the reaction temperature is normally about −30° C. to about 150° C., and is preferably about 0° C. to about 80° C. When using the cerium (IV) salt, the reaction temperature is normally about −30° C. to about 100° C., and is preferably about −20° C. to about 50° C. When using the persulfate salt, the reaction temperature is normally about 20° C. to about 130° C., and is preferably about 50° to about 100° C.

The completion of the reaction can be considered as the disappearance of the N-acyl DOPA derivative [I] or termination of decrease in N-acyl DOPA derivative [I].

After the reaction is completed, the oxazolines [IV] obtained can be separated by pouring the reaction mixture into water and separating the organic layer which may, if desired, be further concentrated. If necessary, in advance of pouring, an aqueous alkaline solution of hydroquinone may be added to the reaction mixture in order to deactivate the residual halogen radical generator, cerium (IV) salt or persulfate salt. The oxazolines [IV] obtained can also be separated, after pouring the reaction mixture into water, by extracting with a known suitable extraction solvents such as toluene, ethyl acetate, and diethyl ether, dichloromethane; and then separating and concentrating the organic layer. The oxazolines [IV] (in or separated from the organic layer) can be further purified by means known to those skilled in the art, including column chromatography.

Products

Oxazolines [IV] obtainable in accordance with our process include racemic and optically active methyl 5-(3,4-dimethoxyphenyl)-2-methyl-2-oxazoline-4-carboxylate, methyl 5-(3,4-dibenzyloxyphenyl)-2-methyl-2-oxazoline-4-arboxylate, methyl 5-(3,4-methylenedioxyphenyl)-2-methyl-2-oxazoline-4-carboxylate, methyl 5-[3,4-(2-propylidenedioxy) phenyl]-2-methyl-2-oxazoline-4-carboxylate, o-benzyl 5-(3,4-dibenzyloxyphenyl)-2-methyl-2-oxazoline-4-carboxylate, benzyl 5-(3,4-dimethoxyphenyl)-2-methyl-2-oxazoline-4-carboxylate, benzyl S-(3,4-dibenzyloxyphenyl)-2-methyl-oxazoline-4-carboxylate, benzyl 5-[3,4-(2-propylidenedioxy)phenyl]-2-methyl-2-oxazoline-4-carboxylate, methyl 5-(3,4-dimethoxyphenyl)-2-phenyl-2-oxazoline-4-carboxylate, methyl 5-(3,4-dibenzyloxyphenyl)-2-phenyl-2-oxazoline-4-carboxylate, methyl 5-(3,4-methylenedioxyphenyl)-2-phenyl-2-phenyl-2-oxazoline4-carboxylate, methyl 5-[3,4-(2-propylidenedioxy)phenyl]-2-phenyl-2-oxazoline4-carboxylate, benzyl 5-(3,4-dimethoxyphenyl)-2-phenyl-2-oxazoline-4-carboxylate, benzyl 5-(3,4-dibenzyloxyphenyl)-2-phenyl-2-oxazoline-4-carboxylate, benzyl 5-[3,4-(2-propylideneoxy)phenyl]-2-phenyl-2-oxazoline-4-carboxylate, methyl 5-(2-chloro-4,5-dimethoxyphenyl)-2-methyl-2-oxazoline4-carboxylate, methyl 5-(2-chloro-4,5-dibenzyloxyphenyl)-2-methyl-2-oxazoline-4-carboxylate, methyl 5-(2-chloro-4,5-methylenedioxyphenyl)-2-methyl-2-oxazoline-4-carboxylate, methyl 5-[2-chloro-4,5-(2-propylidenedioxy)phenyl]-2-methyl-2-oxazoline-4-carboxylate, benzyl 5-(2-chloro-4,5-dimethoxyphenyl)-2-methyl-2-oxazoline-4-carboxylate, benzyl 5-(2-chloro-4,5-dibenzyloxyphenyl)-2-methyl-2-oxazoline-4-carboxylate, benzyl 5-[2-chloro-4,5-(propylidenedioxy)phenyl]-2-methyl-2-oxazoline-4-carboxylate, methyl 5-(2-chloro-4,5-dimethoxyphenyl)-2-phenyl-2-oxazoline-4-carboxylate, methyl 5-(2-chloro-4,5-dibenzyloxyphenyl)-2-phenyl-2-oxazoline-4-carboxylate, methyl 5-(2-chloro-4,5-methylenedioxyphenyl)-2-phenyl-2-oxazoline-4-carboxylate, methyl 5-(2-chloro-4,5-propylidenedioxy)phenyl]-2-phenyl-2-oxazoline-4-carboxylate, benzyl 5-(2-chloro-4,5-dimethoxyphenyl)-2-phenyl-2-oxazoline-4-carboxylate, benzyl 5-(2-chloro-4,5-dibenzyloxyphenyl)-2-phenyl-2-oxazoline-4-carboxylate, benzyl 5-[2-chloro-4,5-(2-propylidenedioxy)phenyl]-2-phenyl-2-oxazoline-4-carboxylate, methyl 5-(2-bromo-4,5-dimethoxyphenyl)-2-methyl-2-oxazoline-4-carboxylate, methyl 5-(2-bromo-4,5-dibenzyloxyphenyl)-2-methyl-2-oxazoline-4-carboxylate, methyl 5-(2-bromo-4,5-(2-methylenedioxyphenyl)-2-methyl-2-oxazoline-4-carboxylate, methyl 5-[2-bromo-4,5-(2-propylidenedioxy)phenyl]-2-methyl-2-oxazoline-4-carboxylate, benzyl 5-(2-bromo-4,5-dimethoxyphenyl)-2-methyl-2-oxazoline-4-carboxylate, benzyl 5-(2-bromo-4,5-dibenzyloxyphenyl)-2-methyl-2-oxazoline-4-carboxylate, benzyl 5-[2-bromo-4,5-(2-propylidenedioxy)phenyl]-2-methyl-2-oxazoline-4-carboxylate, methyl 5-(2-bromo-4,5-dimethoxyphenyl)-2-phenyl-2-oxazoline-4-carboxylate, methyl 5-(2-bromo-4,5-dibenzyloxyphenyl)-2-phenyl-2-oxazoline-4-carboxylate, methyl 5-(2-bromo-4,5-methylenedioxyphenyl)-2-phenyl-2-oxazoline-4-carboxylate, methyl 5-[2-bromo-4,5-(2-propylidenedioxy)phenyl]-2-phenyl-2-oxazoline-4-carboxylate, benzyl 5-(2-bromo-4,5-dimethoxyphenyl)-2-phenyl-2-oxazoline-4-carboxylate, benzyl 5-(2-bromo-4,5-dibenzyloxyphenyl)-2-phenyl-2-oxazoline-4-carboxylate, and benzyl 5-[2-bromo-4,5-(2-propylidenedioxy)phenyl]-2-phenyl-2-oxazoline-4-carboxylate, among others.

Preparation of Threo DOPS [III] from Oxazoline [VI]

Racemic or optically active threo DOPS [III] can be produced from the oxazolines [IV] by opening the oxazoline ring; removing (eliminating) the $R^1$, $R^2$ and $R^3$ protecting groups; and, optionally, removing (eliminating) X when n is 1, 2 or 3.

The opening of the oxazoline ring to form an amino alcohol can be conducted by treating the oxazolines [IV] with an acid reagent containing, for instance, a mineral acid such as hydrochloric acid or sulfuric acid, a lower alkyl carboxylic acid such as formic acid, a halogenated lower alkyl carboxylic acid such as trifluoroacetic acid; an alkyl-sulfonic acid such as methanesulfonic acid, or mixtures thereof, in a suitable solvent. Examples of suitable solvents include, for instance, water, water-containing methanol, or water-containing acetone, among others.

The elimination of $R^1$ and $R^2$ can be conducted in various manners. When $R^1$ and $R^2$ represent an alkyl group or $R^1$ and $R^2$ can together represent a non-substituted methylene group, they can be removed, e.g. eliminated, by treating the compound containing $R^1$ and $R^2$ with a Lewis acid such as aluminum chloride, titanium tetrachloride, boron trifluoride. When $R^1$ and $R^2$ represent an aralkyl group or when $R^1$ and $R^2$ are combined together to represent a methylene group substituted with an aryl group, they can be removed, e.g. eliminated, effectively by hydrogenolysis in the presence of a noble metal catalyst, such as palladium, rhodium, or platinum, or mixtures thereof. When $R^1$ and $R^2$ represent an aryl group, they can be eliminated effectively by treating the compound containing $R^1$ and $R^2$ with palladium in the presence of p-toluenesulfonic acid catalyst. When $R^1$ and $R^2$ combine together to represent a methylene group substituted with two alkyl groups or an alkylene group, their removal, e.g. elimination, by hydrolysis under an acid condition is effective.

When $R^3$ is an alkyl group or an aryl group, $R^3$ can be eliminated, for example, by treating the compound containing $R^3$ with an aqueous alkaline solution of a metal hydroxide, such as lithium hydroxide, sodium hydroxide, or barium hydroxide, or by treating the compound containing $R^3$ with an acid, such as hydrochloric acid, sulfuric acid, or nitric acid. When $R^3$ is an aralkyl group, $R^3$ can be eliminated, for example, by hydrogenolyzing in the presence of a noble metal catalyst, such as palladium, rhodium and/or platinum. When $R^3$ is an allyl group, $R^3$ can be eliminated, for example, by a treatment with tetrakis (triphenylphosphine)palladium.

When n is 1 to 3, threo DOPS [III] can be produced by eliminating halogen of a precursor substituted with halogen due to hydrogenolysis in the presence of a nobel metal catalyst, such as palladium, rhodium and/or platinum.

Our process offers flexibility in effecting the ring opening and de-blocking, e.g. removing protecting groups etc. For instance, the opening of the oxazoline ring and removal of the $R^3$ protecting group can be simultaneously conducted, followed by removal of the $R^1$ and $R^2$ protecting groups. The $R^1$ and $R^3$ protecting groups can also be removed, followed by simultaneous ring opening and removal of the $R^3$ protecting group. Alternatively, the ring opening and removal of the $R^1$, $R^2$ and $R^3$ protecting groups can simultaneously be effected.

Preparation of N-acyl DOPA Derivative [I] from DOPA [A]

The N-acyl DOPA derivative [I] can be produced, for example, by the process described below.

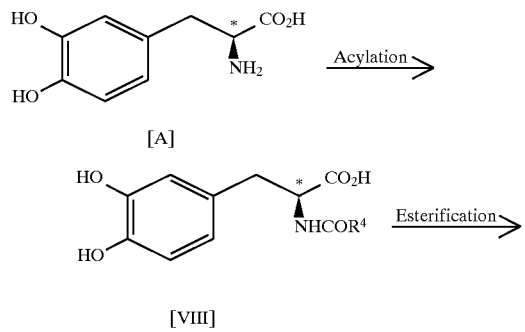

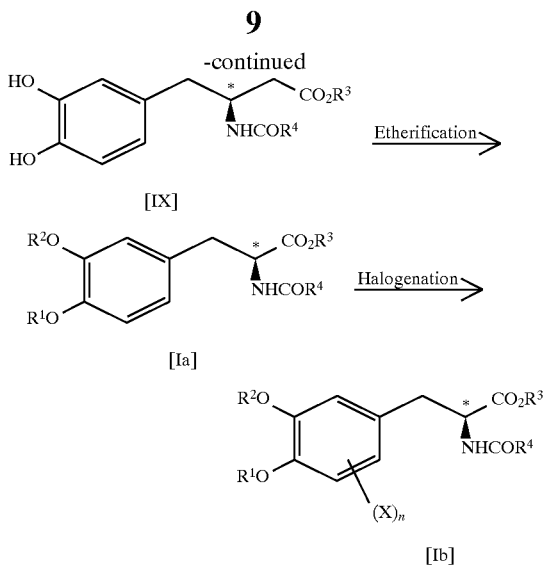

Step (1): Synthesis of compound [VIII] by Acylating DOPA [A]

The compound [VIII] can be produced by reacting DOPA [A] with an acylating agent in the presence of a base. Suitable acylating agents include, for instance, a derivative of carboxylic acid represented by $R^4COOH$ such as, for example, an acid halide such as an acid chloride or an acid bromide; an acid anhydride; or an acid imidazolide. The acylating agent is normally used in an amount of about 0.1 to about 20 mol, preferably about 1 to about 4 mol, based on 1 mol of DOPA [A]. Suitable bases include inorganic bases such as alkali metal hydroxides including sodium hydroxide, potassium hydroxide, and lithium hydroxide, and organic bases such as triethylamine, tributylamine, and/or pyridine. The base is normally used in an amount of about 1 to about 100 mol, preferably about 3 to about 20 mol, based on 1 mol of DOPA [A].

The acylation is conducted in the presence or absence of a solvent. Suitable solvents include solvents which are inactive to the reaction such as, for example, aromatic hydrocarbons including toluene and xylene; hydrocarbon halides including dichloromethane, chloroform, monochlorobenzene, and 1,2-dichloroethane; ketones including acetone, and methyl ethyl ketone; esters including ethyl acetate, butyl acetate, and methyl acetate; water; or any mixture thereof. When the reaction is conducted in the presence of a solvent, the solvent is generally used in an amount of about 1- to about 50-fold, preferably about 1- to about 10-fold, by weight, based on the DOPA [A].

The reaction temperature is normally about −50° C. to about 100° C., but is preferably about −20° C. to about 60° C. Disappearance of DOPA [A] or termination of a further decrease in DOPA [A] can be considered to be the completion of the reaction. This disappearance of DOPA [A] or the termination of a further decrease in DOPA [A] can be easily determined, for example, by high performance liquid chromatography or thin layer chromatography.

After the reaction is completed, a compound [VIII] can be obtained by concentrating the reaction solution, pouring the concentrated solution into water, adding a mineral acid such as hydrochloric acid, sulfuric acid or the like or an organic acid such as acetic acid, methanesulfonic acid, or the like, to liberate the compound [VIII]; and separating out the compound [VIII]. After pouring into water the compound [VIII] can also be obtained by extracting with a solvent such as toluene, ethyl acetate, dimethyl ether, dichloromethane, or the like; partitioning the obtained organic layer; and concentrating the partitioned organic layer. If necessary, the compound [VIII] can also be purified using techniques known to the person skilled in the art, such as by subjecting recovered compound [VIII] to recrystallization, column chromatography, or the like.

Step (2): Synthesis of Compound [IX] due to Esterification of Compound [VIII]

The compound [IX] can be produced by esterifying the compound [VIII].

The esterification is conducted, for example, by reacting the compound [VIII] with at least one alcohol represented by $R^3OH$ in the presence of an activating agent or an acid catalyst. $R^3$ is as described elsewhere herein. The alcohols are normally used in an amount of about 0.1 to about 100 mol, preferably about 1 to about 50 mol, based on 1 mol of the compound [VIII]. Suitable activating agents include, for example, thionyl chloride, phosphorous trichloride, oxalyl chloride, and the like. The activating agent is used in an amount of about 1 to about 50 mol, preferably about 1 to about 10 mol, based on 1 mol of the compound [VII]. An acid catalyst, such as hydrochloric acid, sulfuric acid, p-toluenesulfonic acid, and the like, can also be used in lieu of the activating agent. The acid catalyst is used in an amount of about 0.001 to about 10 mol, preferably about 0.01 to about 1 mol, based on 1 mol of the compound [VIII]. A strong acidic ion exchange resin, such as Amberlyst-15 (Rohm & Haas), can also be used as the acid catalyst. The reaction can be accelerated by removing water formed in the reaction by azeotropic distillation or by using a dehydrating agent such as sulfuric acid, anhydrous calcium chloride, molecular sieves, and the like.

The esterification can be conducted in the presence or absence of a solvent. Suitable solvents include solvents which are inactive to the reaction such as, for example, aromatic hydrocarbon, hydrocarbon halide, ketone, esters or a mixture thereof, which are the same as those described elsewhere hereinabove. When the reaction is conducted in the presence of the solvent, the solvent is normally used in an amount of about 1- to about 50-fold by weight, preferably about 1- to about 10-fold, based on the weight of the compound [VIII].

The reaction temperature is normally about −50° C. to about 100° C., preferably about −20° C. to about 60° C. Disappearance of the compound [VIII] or termination of a further decrease in the compound [VIII] can be considered to be the completion of the reaction.

After the reaction is completed, a compound [IX] can be obtained in diverse manners. For example, it can be obtained by concentrating the reaction solution, pouring the concentrated solution into water and then separating the organic layer to obtain the compound [IX]. A compound [IX] can also be obtained by extracting the reaction solution (or a concentrate thereof) with the same extraction solvent as that described above, partitioning and concentrating the organic layer. If necessary, a compound [IX] can also be purified by subjecting the recovered compound [IX] to recrystallization, column chromatography, and the like, as described above.

Our process provides further flexibility in that the compound [IX] can also be produced by interchanging the steps of (1) and (2), that is, protecting a carboxyl group first and then protecting an amino group.

Step (3): Synthesis of Compound [Ia] through Etherification of Compound [IX]

The compound [Ia] is a compound [I] wherein n is 0. The compound [Ia] can be produced by etherifying the compound [IX]. The reaction conditions for etherification may vary depending on the type of the etherifying agent to be used.

When an alkyl group, an aralkyl group or an allyl group is introduced as $R^1$ and $R^2$ by etherification, alkyl halide, aralkyl halide, sulfonates, and the like, can be used as the etherifying agent. The etherifying agent is normally used in an amount of abut 0.1 to about 20 mol, preferably about 2 to 10 mol, based on 1 mol of the compound [IX]. When using such an etherifying agent, the etherification is conducted by reacting the compound [IX] with the etherifying agent in the presence of a base. Suitable bases include, for example, inorganic bases including bases containing alkali metal cations such as sodium carbonate, potassium carbonate, sodium hydroxide, potassium hydroxide, lithium hydroxide, and the like and organic bases such as triethylamine, tributylamine, pyridine, and the like. The base is normally used in an amount of about 1 to about 100 mol, preferably about 2 to about 20 mol, based on 1 mol of the compound [IX].

When an optionally substituted methylene group is introduced by the etherification, suitable etherifying agents include, for example, ketones such as acetone, cyclohexanone, benzophenone, and the like, acetals such as 1,1-dimethoxyethane, 2,2-dimethoxypropane, and the like and olefins such as 2-methoxypropene, and the like. The etherifying agent is normally used in an amount of about 1 to about 20 mol, preferably about 1 to about 10 mol, based on the compound [IX]. When using such a etherifying agent, the etherification is normally conducted by reacting the compound [IX] with the etherifying agent in the presence of an acid catalyst. As the acid catalyst, hydrochloric acid, sulfuric acid, p-toluenesulfonic acid, etc. are used. The acid catalyst is normally used in an amount of about 0.001 to about 10 mol, preferably about 0.01 to about 1 mol, based on 1 mol of the compound [IX]. As the acid catalyst, a strong acidic ion exchange resin, such as described elsewhere herein, can also be used.

When using any type of an etherifying agent, the etherification is conducted in the presence or absence of a solvent. Suitable solvents include those which are inactive to the reaction such as, for example, aromatic hydrocarbons, hydrocarbon halides, ketones, esters or a mixture thereof, which are the same as those described elsewhere herein. When the reaction is conducted in the presence of the solvent, the solvent is used in an amount of about 1 to 50-fold by weight, preferably about 1- to about 10-fold by weight, based on the compound [IX].

The reaction temperature is normally about −50° C. to about 100° C., preferably about −20° C. to about 60° C. Disappearance of the compound [IX] or termination of a further decrease in compound [IX] can be considered to be the completion of the reaction.

After the reaction is completed, a compound [Ia] can be obtained by diverse means. For example, the reaction solution can be concentrated, poured into water and then the organic layer separated out. The compound [Ia] can also be obtained by extracting the reaction solution with the same extraction solvent as that described above, partitioning and concentrating the organic layer. If necessary, the compound [Ia] can also be purified by techniques familiar to a person skilled in the art, such as subjecting compound [Ia] to recrystallization, column chromatography, and the like.

When the protecting groups $R^1$, $R^2$ and $R^3$ are the same, the compound [Ia] can also be produced from DOPA [A] via two steps by conducting the above step (3) using the compound [VIII] in place of the compound [IX] without conducting the above step (2). In this case, alkyl halide (such as alkyl iodide or alkyl bromide), aralkyl halide (such as aralkyl iodide or alkyl bromide), and/or sulfonates, as described above, can be used as the esterifying/etherifying agent. The esterifying/etherifying agent is normally used in an amount of about 0.1 to about 20 mol, preferably about 3 to about 10 mol, based on 1 mol of the compound [VIII]. When using the esterifying/etherifying agent, the esterification/etherification is normally conducted by reacting the compound [VIII] with the esterifying/etherifying agent in the presence of a base. Suitable bases include inorganic bases such as bases containing alkali metal cations including sodium carbonate, potassium carbonate, sodium hydroxide, potassium hydroxide, and/or lithium hydroxide; and organic bases such as triethylamine, tributylamine, and/or pyridine. The base is normally used in an amount of abut 1 to about 100 mol, preferably about 3 to about 20 mol, based on 1 mol of the compound [VIII]. The reaction is conducted in the presence or absence of a solvent. Suitable solvents include those which are inactive to the reaction such as, for example, aromatic hydrocarbon, hydrocarbon halide, ketones, esters, or a mixture thereof, which are the same as those described above. When the reaction is conducted in the presence of the solvent, the solvent is normally used in an amount of about 1- to about 50-fold by weight, preferably about 1- to about 10-fold by weight, based on the compound [VIII].

The reaction temperature is normally about −50° C. to about 100° C., preferably about −20° C. to about 60° C. Disappearances of the compound [VIII] or termination of decrease a further in compound [VIII] can be considered to be the completion of the reaction.

After the reaction is completed, a compound [Ia] can be obtained by diverse means. For instance, it can be obtained by concentrating the reaction solution, pouring the concentrated solution into water and then separating out the organic layer. The compound [Ia] can also be obtained by extracting the reaction solution with the same extraction solvent as that described above, partitioning and concentrating the organic layer. If necessary, the compound [Ia] can also be purified by techniques familiar to those skilled in the art, such as by subjecting to recrystallization, column chromatography, and the like.

Step (4): Synthesis of Compound [Ib] by Halogenating Compound [Ia]

The compound [Ib] is a compound [I] wherein n is 1, 2 or 3. The compound [Ib] can be produced by halogenating the compound [Ia].

The halogenation is conducted by reacting the compound [Ia] with a halogenating agent. Suitable halogenating agents include, for example, a halogen-containing inorganic acid salt such as sodium chlorate, sodium chlorite, sodium hypochlorite, potassium chlorate, potassium hypochlorite, and the like; a halogen source such as molecular chlorine and molecular bromine, a N-halosuccinimide such as N-chlorosuccinimide or N-bromosuccinimide, 1,3-dibromo-5,5-dimethylhydantoin, and/or 5-bromo-2,2-dimethyl-1,3-dioxane-4,6-dione. The halogenating agent is normally used in an amount of about 0.5 to about 100 mol, preferably about 1 to about 20 mol, based on 1 mol of the compound [Ia].

The halogenation is conducted in the presence or absence of a solvent. Suitable solvents include those which are inactive to the reaction such as, for example, hydrocarbon halides which are the same as those described above, nitrites such as lower alkyl nitriles including acetonitrile and/or propionitrile; organic acids including lower alkyl carboxylic acids such as acetic acid and/or propionic acid; water; or a mixture of any thereof. When the reaction is conducted in the presence of the solvent, the solvent is used in an amount of about 1- to about 50-fold by weight, preferably about 1- to about 10-fold by weight, based on the compound [Ia].

The reaction temperature is normally about −50° C. to about 100° C., preferably about −20° C. to about 60° C. Disappearance of the compound [Ia] or termination of decrease in compound [Ia] can be considered to be the completion of the reaction.

After the reaction is completed, a compound [Ib] can be obtained by diverse means. For example, it be obtained by inactivating the residual halogenating agent with sodium thiosulfate, hydroquinone, and/or sodium sulfite; concentrating the reaction solution, pouring the concentrated solution into water; and then separating out the organic layer. The compound [Ib] can also be obtained by extracting the reaction solution with the same extraction solvent as that described above, partitioning and concentrating the organic layer. If necessary, the compound [Ib] can also be purified by techniques familiar to those skilled in the art including subjecting compound [Ib] to recrystallization, column chromatography, and the like.

As described above, the novel N-acyl DOPA derivative [I] and oxazolines [IV] of the present invention are extremely important intermediates of threo DOPS [III] as the drug. The oxazolines [IV] of the present invention can be produced from the N-acyl DOPA derivative [I] in one stage according to the process of the present invention. The threo DOPS [III] can be readily produced from the oxazolines [IV] of the present invention by a few steps, such as one having two to three steps.

The optically active form of L-threo DOPS [III] is generally more effective as a drug than the D-threo DOPS [III] and the racemic form of the threo DOPS [III]. Thus, the L-DOPA derivative is preferred.

The present novel compounds and methods for their synthesis are described in Japanese Application 07-119864 filed May 18, 1995 and in Japanese Application 07-119865 filed May 18, 1995, the complete disclosures of which are incorporated herein by reference.

EXAMPLES

The following Examples further illustrate the present invention in detail but are not to be construed to limit the scope thereof.

Example 1

Production of N-acyl DOPA Derivative [Ia]

(1) Acylation

To a solution of sodium hydroxide (85.0 g 2.13 mol) and water (500 g), L-DOPA ((2S)-2-amino-3-(3,4-dihydroxyphenyl)propanoic acid) (100 g, 0.51 mol) was added at −10° C. to 0° C. while stirring the solution. Then, benzoyl chloride (71.3 g, 0.52 mol) was added dropwise at the same temperature (−10° C. to 0° C.) over 3 hours and the mixture was heated to room temperature, about 25° C., over 6 hours.

Then, 1N-hydrochloric acid was added to adjust the pH to 1.0 and the liberated organic substance was extracted with ethyl acetate. The organic layer was washed with saturated saline solution, dried over anhydrous magnesium sulfate and then concentrated under reduced pressure to obtain 145.0 g (0.48 mol, yield: 95%) of (2S)-2-benzoylamino-3-(3,4-dihydroxyphenyl)propanoic acid.

$^1$H-NMR ($\delta$):3.00 (dd, 1H, J=8.6 Hz, 13.9 Hz), 3,18(dd, 1H, J=5.1 Hz, 13.9 Hz), 4.79(dd, 1H, J=5.1 Hz, 8.6 Hz), 4.88(brs, 4H), 6.57–6.61(m, 1H), 6.67–6.73 (m, 2H), 7.38–7.54 (m, 3H), 7.71–7.82(m, 2H)

(2) Esterification

To a solution of (2S)-2-benzoylamino-3-(3,4-dihydroxyphenyl)propanoic acid (93.9 g, 0.315 mol) and methanol (400 ml), thionyl chloride (74.2 g, 0.624 mol) was added dropwise while stirring the solution. After stirring at the same temperature (−10° C. to 0° C.) for one hour, the mixture was heated to room temperature over 12 hours.

Then, the reaction mixture was concentrated by distilling off the residual thionyl chloride and methanol under reduced pressure to obtain a liquid residue. The residue was extracted by adding water and ethyl acetate, and then the organic layer was washed with saturated saline solution, dried over anhydrous magnesium sulfate and then concentrated under reduced pressure to obtain 97.2 g (0.308 mol, yield 99%) of methyl (2S)-2-benzoylamino-3-(3,4-dihydroxyphenyl)propanoate.

$^1$H-NMR ($\delta$):2.97–3.05(m, 1H), 3.06–3.14(m, 1H), 3.69 (s, 3H), 4.92–5.00 (m, 1H), 6.40–6.50 (m, 1H), 6.67–6.84 (m, 3H), 6.97(brs, 2H), 7.26–7.47 (m, 3H), 7.63–7.67 (m, 2H)

(3) Etherification

A mixture of methyl (2S)-2-benzoylamino-3-(3,4-dihydroxyphenyl)propanoate (3.15 g, 10.0 mmol), methyl iodide (2.98 g, 21.0 mmol), potassium carbonate (2.9 g, 21.0 mmol) and acetone (20 ml) was refluxed and stirred for 8 hours.

The reaction mixture was filtered and the filtrate was concentrated under reduced pressure to obtain a liquid residue. The residue was treated with silica gel chromatography to obtain 3.38 grams (9.9 mmol, yield: 99%) of methyl (2S)-2-benzoylamino-3-(3,4-dimethoxyphenyl)propanoate.

$^1$H-NMR ($\delta$):3.11–3.29 (m, 2H), 3.75 (s, 3H), 3.77 (s, 3H), 3.85 (s, 3H), 5.00–5.09 (m, 1H), 6.63–6.83 (m, 4H), 7.38–7.53 (m, 3H), 7.66–7.75 (m, 2H).

Example 2

Production of N-acyl DOPA Derivative [Ia]

The procedure of Example 1 part (3) was repeated, except that benzyl bromide (3.59 g, 21.0 mmol) was used instead of methyl iodide, and 4.76 g (20.2 mmol, yield: 96%) of methyl (2S)-2-benzoylamino-3-(3,4-dibenzyloxyphenyl) propanoate was obtained.

FD-MS: 495

$^1$H-NMR ($\delta$):3.05 (m, 2H), 3.68 (s, 3H), 4.95 (m, 1 H), 5.05–5.11 (m, 4H), 6.53 (dd, 1H, J=2.0 Hz, 8.2 Hz), 6.70–7.81 (m, 3H), 7.24–7.50 (m, 13H), 7.65 (m, 2H)

Example 3

Production of N-acyl DOPA Derivative [Ia]

The procedure of Example 1 part (3) was repeated, except that methylene iodide, and (2.68 g, 10.0 mmol) was used instead of methyl iodide, and 1.93 g (5.90 mmol, yield: 59%) of methyl (2S)-2-benzoylamino-3-(3,4-methylenedioxyphenyl)propanoate was obtained.

$^1$H-NMR ($\delta$):3.08–3.24 (m, 2H), 3.76 (s, 3H), 4.99–5.07 (m, 1H), 5.91 (s, 2H), 6.55–6.73 (m, 4H), 7.38–7.49 (m, 3H), 7.72–7.77 (m, 2H)

Example 4

Production of N-acyl DOPA Derivative [1a]

To a solution of methyl (2S)-2-benzoylamino-3-(3,4-dihydroxyphenyl)propanoate (3.23 g, 10.2 mmol), p-toluenesulfonic acid monohydrate (195 mg, 1.03 mmol) and chloroform (100ml), 2-methoxypropene (886 mg, 12.3 mmol) were added dropwise at room temperature over 30 minutes. This solution was heated to 40° C. and stirred at the same temperature (40° C.) for 8 hours.

The resultant reaction mixture was concentrated under reduced pressure to obtain a liquid residue. The residue was then dissolved in ethyl acetate and the resulting solution was washed in turn with an aqueous saturated sodium bicarbonate solution, water and saturated saline solution. The organic layer was washed dried over anhydrous sodium sulfate and then concentrated under reduced pressure to obtain a crude product. This crude product was treated with silica gel chromatography and 3.10 g (yield: 85%) of methyl (2S)-2-benzoylamino-3-[3,4-(dimethylenedioxy)propanoate was obtained.

$^1$H-NMR ($\delta$):1.65 (s, 6H), 3.08–3.23 (m, 2H), 3.77 (s, 3H), 4.98–5.04 (m, 1H), 6.51–6.66 (m, 4H), 7.38–7.53 (m, 3H), 7.71–7.76 (m, 2H)

Example 5

Production of N-acyl DOPA Derivative [Ia]

The procedure of Example 1 part (3) was repeated, except that (2S)-2-benzoylamino-3-(3,4-dihydroxyphenyl) propanoic acid (1.53 g, 5.1 mmol) was used instead of methyl (2S)-2-benzoylamino-3-(3,4-dihydroxyphenyl) propanoate, and benzyl bromide (3.59 g, 21.0 mmol) was used instead of methyl iodide, and 2.85 g (5.0 mmol, yield: 98%) of benzyl (2S)-2-benzoylamino-3-(3,4-dibenzyloxyphenyl)propanoate was obtained.

FD-MS:571

$^1$H-NMR ($\delta$):3.10 (m, 2H), 4.96 (s, 1H), 5.04–5.10 (m, 6H), 6.54 (dd, 1H, J=2.0 Hz, 8.2 Hz), 6.77–7.70 (m, 23H)

Example 6

Production of N-acyl DOPA Derivative [Ia]
(1) Esterification

To a solution of (2S)-2-benzoylamino-3-(3,4-dihydroxyphenyl)propanoic acid (5.00 g, 15.9 mmol) and chloroform (50 ml), thionyl chloride (2.26 g, 19.0 mmol) was added dropwise at −10° to 0° C. with stirring. After stirring at the same temperature (−10° TO 0° C.) for 30 minutes, benzylalcohol (2.06 g, 19.1 mmol) was added dropwise at the same temperature. After stirring at the same temperature for one hour, the mixture was heated to room temperature over 12 hours.

Then, the resultant reaction mixture was concentrated under reduced pressure to obtain a residue in the form of a gel. The residue was extracted by adding water and ethyl acetate. The organic layer obtained was washed with saturated saline solution, dried over anhydrous magnesium sulfate and then concentrated under reduced pressure to obtain 5.90 g (15.1 mmol, yield: 95%) of benzyl (2S)-2-benzoylamino-3-(3,4-dihydroxyphenyl)propanoate.

$^1$H-NMR ($\delta$):3.10 (m, 2H), 4.95 (s, 2H), 5.04–5.10 (m, 1H), 6.70–7.68 (m, 16H)
(2) Etherification The procedure of Example 1 part (3) was repeated, except that benzyl (2S)-2-benzoylamino-3-(3,4-dihydroxyphenyl) propanoate (3.91 g, 10.0 mmol) and using benzyl bromide (3.59 g, 21.0 mmol) was used instead of methyl iodide, and 5.6 g(9.8 mmol, yield: 98%) of benzyl (2S)-2-benzoylamino-3-(3,4-dibenzyloxyphenyl)propanoate was obtained.

Example 7

Production of N-acyl DOPA Derivative [Ia]

The procedure of Example 1 was repeated, except that acetyl chloride (40.0 g, 0.51 mmol) was used instead of benzyol chloride, and 87.5 g (0.31 mmol, total yield: 61%) of methyl (2S)-2-acetylamino-3-(3,4-dihydroxyphenyl) propanoate was obtained.

$^1$H-NMR ($\delta$): 1.98 (s, 3H), 3.10–3.29 (m, 2H), 3.74 (s, 3H), 3.77 (s, 3H), 3.85 (s, 8H), 4.80–4.91 (m, 1H), 6.65–6.88 (m, 4H)

Example 8

Production of N-acyl DOPA Derivative [Ib]

To a solution of an acetic acid-acetonitrile (1:1) solution (100 ml) and methyl (2S)-2-benzoylamino-3-(3,4-dimethoxyphenyl)propanoate (2.0 g, 5.82 mmol), an aqueous 10% sodium hypochlorite solution (4.96 g, 6.66 mmol) was added dropwise while stirring with ice cooling over one hour, and then the mixture was stirred continuously for one hour.

An aqueous sodium thiosulfate solution was added to deactivate the residual sodium hypochlorite and the mixture was concentrated under reduced pressure to obtain a residue in the form of a gel. The residue obtained was treated with silica gel chromatography and 1.58 g(4.18 mmol, yield 72%) of methoxy (2S)-2-benzoylamino-3-(2-chloro-4,5-dimethoxyphenyl)propanoate.

$^1$H-NMR ($\delta$: 3.24–3.43 (m, 2H), 3.73 (s, 3H), 3.77 (s, 3H), 3.84 (s, 3H), 5.00–5.08 (m, 1H), 6.70 (s, 1H), 6.72–6.82 (m, 1H), 6.84 (s, 1H), 7.38–7.53 (m, 3H), 7.73–7.76 (m, 2H)

Example 9

Production of N-acyl DOPA Derivative [Ib]

The procedure of Example 8 was repeated, except that methyl (2S)-2-benzoylamino-3-[3,4-(dimethylmethylenedioxy)phenyl]propanoate (2.07g, 5.82 mmol) was used instead of methyl (2S)-2-benzoylamino-3-(3,4-dimethoxyphenyl)propanoate, and 1.95 g (5.00 mmol, yield: 86%) of methyl (2S)-2-benzoylamino-3-[2-chloro-4.5-(dimethylmethylenedioxy)phenyl]propanoate was obtained.

$^1$H-NMR ($\delta$): 1.64 (s, 6H), 3.17–3.35 (m, 2H), 3.77 (s, 3H), 4.95–5.05 (m, 1H, 6.61 (s, 1H), 6.73 (s, 1H), 6.76 (brs. 1H), 7.38–7.53 (m, 3H), 7.73–7.77 (m, 2H)

Example 10

Production of N-acyl DOPA Derivative [Ib]

The procedure of Example 8 was repeated, except that methyl (2S)-2-acetylamino-3-(3,4-dimethoxyphenyl) propanoate (1.64 g, 5.82 mmol) was used instead of methyl (2S)-2-benzoylamino-3-(3,4-dimethoxyphenyl)propanoate, and 1.29 g (4.07 mmol, yield: 70%) of methyl (2S)-2-acetylamino-3-(2-chloro-4,5-dimethoxyphenyl)propanoate was obtained.

$^1$H-NMR ($\delta$): 1.99 (s, 3H), 3.10–3.29 (m, 2H), 3.74 (s, 3H), 3.82 (s, 3H), 3.86 (s, 3H), 4.83 4.91 (m, 1H), 6.10–6.19 (m, 1H), 6.71 (s, 1H), 6.84 (s, 1H)

Example 11

Production of N-acyl DOPA Derivative [1 b]

The procedure of Example 8 was repeated, except that methyl (2S)-2-benzoylamino-3-(3,4-methylenedioxyphenyl)propanoate (1,91 g, 5.82 mmol) was used instead of methyl (2S)-2-benzoylamino-3-(3,4- dimethoxyphenyl)propanoate, and 1.64 g (4.54 mmol, yield: 78%) of methyl (2S)-2-benzoylamino-3-(2-chloro-4,5-methylenedioxyphenyl)propanoate was obtained.

¹H-NMR (δ): 3.24–3.44 (m, 2H), 3.75 (s,3H), 5.02–5.10 (m, 1H), 5.94 (s, 2H), 6.70 (s, 1H), 6.73–6.83 (m, 1H), 6.84 (s, 1H), 7.38–7.49 (m, 3H), 7.73–7.77 (m, 2H)

Example 12

Production of Oxazoline [IV]

To a solution of methyl (2S)-2-benzoylamino-3-(3,4-dimethoxyphenyl)propanoate (100 mg, 0.291 mmol) and carbon tetrachloride (10 ml), N-bromosuccinimide (52 mg, 0.29 mmol) was added and 2,2'-azobis(2,4-dimethylvaleonitrile) (7 mg. 0.028 mmol) was further added while stirring the solution at room temperature. The mixture was heated to 70° C. and then stirred at the same temperature (−10° C. to 0° C.) for 30 minutes.

After cooling to room temperature, the resultant reaction mixture was concentrated under reduced pressure to obtain a residue in the form of a gel. The residue was extracted by adding water and ethyl acetate. The organic layer was washed with saturated saline solution, dried over anhydrous sodium sulfate and then concentrated under reduced pressure. The residue was treated with silica gel chromatography and 24.8 mg(0.073 mol, yield: 25%) of methyl (4S,5R)-5-(3,4-dimethoxyphenyl)-2-phenyl-2-oxazoline-4-carboxylate was obtained.

¹H-NMR (δ): 3.85 (s, 3H), 3.87 (s, 3H), 3.88 (s, 3H), 4.84 (d, 1H, J=7.6 Hz), 5.84 (d, 1H, J=7.6 Hz), 6.81–7.06 (m, 3H), 7.41–7.54 (m, 3H), 8.04–8.08 (m, 2H)

Example 13

Production of Oxazoline [IV]

The procedure of Example 12 was repeated, except that methyl (2S)-2-benzoylamino-3-(2-chloro-4,5-dimethoxyphenyl)propanoate (110 mg, 0.291 mmol) was used instead of methyl (2S)-2-benzoylamino-3-(3,4-dimethoxyphenyl)propanoate, 81 mg (0.25 mmol, yield: 74%) of methyl (4S, 5R)-5-(2chloro-4,5-dimethoxyphenyl)-2-phenyl-2-oxazoline-4-carboxylate was obtained.

¹H-NMR (δ): 3.79 (s, 3H), 3.85 (s, 3H), 3.88 (s, 3H), 4.78 (d, 1H, J=6.9 Hz), 6.22 (d, 1H, J=6.9 Hz), 6.83 (s, 1H), 6.90 (m, 1H), 7.42–7.58 (m, 3H), 8.05–8.09 (m, 2H)

Example 14

Production of Oxazoline [IV]

The procedure of Example 13 was repeated, except that 2,2'-azobis(4-methoxy-2,4-dimethylvaleronitrile)(8.6 mg, 0.028 mmol) was used instead of 2,2'-azobis(2,4-dimethylvaleronitrile), and the reaction temperature was set at 40° C., and 94 mg (0.25 mmol, yield: 86%) of methyl (4S, 5R)-5-(2-chloro-4,5-dimethoxyphenyl)-2-phenyl-2-oxazoline-4-carboxylate was obtained. The NMR data obtained was the same as that of Example 13.

Examples 15–19

Production of Oxazoline [IV]

The procedure of Example 14 was repeated, except that the compound [I] in Table 1 was used instead of methyl (2S)-2-benzoylamino-3-(2-chloro-4,5-dimethoxyphenyl) propanoate, and the oxazoline [IV] in Table 1 was obtained.

TABLE 1

| Example No. | Compound [I] | Oxazoline [IV] | Yield (%) |
|---|---|---|---|
| 15 | methyl(2S)-2-benzoylamino-3-[3,4-(dimethylmethylenedioxy)phenyl]propanoate | methyl(4S,5R)-5-[3,4(dimethylmethylenedioxy)phenyl]-2-phenyl]-2-oxazoline-4-carboxylate | 59 |
| 16 | methyl(2S)-2-benzoylamino-3-[2-chloro-4,5-(dimethylmethylenedioxy)phenyl]propanoate | methyl(4S,5R)-5-[2-chloro-4,5(dimethylmethylenedioxy)phenyl]-2-phenyl-2-oxazoline-4-carboxylate | 78 |
| 17 | methyl(2S)-2-acetylamino-3-(2-chloro-4,5-dimethoxyphenyl)propanoate | methyl(4S,5R)-5-(2-chloro-4,5-dimethoxyphenyl)-2-methyl-2-oxazoline-4-carboxylate | 51 |
| 18 | methyl(2S)-2-benzoylamino-3-(3,4-methylenedioxyphenyl)propanoate | methyl(4S,5R)-5-(3,4-methylenedioxyphenyl)-2-phenyl-2-oxazoline-4-carboxylate | 35 |
| 19 | methyl(2S)-2-benzoylamino-3-(2-chloro-4,5-methylenedioxyphenyl]propanoate | methyl(4S,5R)-5-(2-chloro-4,5-methylenedioxyphenyl)-2-phenyl-2-oxazolIne-4-carboxylate | 52 |

¹H-NMR (δ) data of methyl (4S,5R)-5-[3,4-(dimethylmethylenedioxy)phenyl]-2-phenyl-2-oxazoline-4-carboxylate: 1.64 (s, 3H), 1.65 (s, 3H), 3.85 (s, 3H), 4.70 (d, 1H, J=6.3 Hz), 6.19 (d, 1H, J=6.3 Hz), 6.70–7.00 (m, 3H), 7.41–7.61 (m, 3H), 8.00–8.09 (m, 2H)

¹H-NMR (δ) data of methyl (4S,5R)-5-[2-chloro-4,5-(dimethylmethylenedioxy)phenyl]-2-phenyl-2-oxazoline-4-carboxylate: 1.64 (s, 3H), 1.65 (s, 3H), 3.84 (s, 3H), 4.72 (d, 1H, J=6.6 Hz), 6.21 (d, 1H, J=6.6 Hz), 6.71 (s, 1H), 6.78 (s, 1H), 7.41–7.60 (m, 3H), 8.00–8.08 (m, 2H)

¹H-NMR (δ)data of methyl (4S,5R)-5-[2-chloro-4,5-(dimethylmethylenedioxy)-2-methyl-2-oxazoline-4-carboxylate: 2.16 (s, 3H), 3.82 (s, 3H), 3.87 (s, 3H), 3.89 (s, 3H), 4.56 (d, 1H, J=7.2 Hz), 6.00 (d, 1H, J=7.2 Hz), 6.76 (s, 1H), 6.88 (s, 1H)

¹H-NMR (δ)data of methyl (4S,5R)-5-(3,4-methylenedioxyphenyl)-2-phenyl-z-oxazoline-4-carboxylate: 3.86 (s, 3H), 4.69 (d, 1H, J=6.3 Hz), 5.97 (s, 2H), 6.19 (d, 1H, j=6.3 Hz), 6.80–7.10 (m, 3H), 7.42–7.58 (m, 3H), 8.04–8.08 (m, 2H)

¹H-NMR (δ)data of methyl (4S,5R)-(2-chloro-4,5-methylenedioxyphenyl)-2-phenyl-2-oxazoline-4-carboxylate: 3;85 (s, 3H), 4.71 (d,1H, J=6.6 Hz), 5.98 (s, 2H), 6.21 (d, 1H, 6.6 Hz), 6.81 (s, 1H) 6.88 (2, H), 7.42–7.58 (m 3H), 8.04–8.08 (m, 2H)

Example 20

Production of Oxazoline [IV]

A mixture of methyl (2S)-2-benzoylamino-3-(3,4-dibenzyloxyphenyl)propanoate (1.98 g, 4.00 mmol), copper sulfate (0.13 g, 0.82 mmol), ammonium persulfate (1.83 g, 8.02 mmol), acetonitrile (60 g) and water (60 g) was stirred at 60° C. for 2 hours.

Then, the low-boiling point component was distilled off and, after extracting with ethyl acetate (100 ml), the organic layer was washed with saturated saline solution, dried over anhydrous sodium sulfate and concentrated under reduced pressure to obtain a residue. The residue was treated with silica gel chromatography and 1.3 g (2.6 mmol, yield: 66%) of methyl (4S,5R)-5-(3,4-dibenzyloxyphenyl)-2-phenyl-2-oxazoline-4-carboxylate was obtained.

FD-MS: 493

$^1$H-NMR (δ): 3.79 (s, 3H), 4.78 (d, 1H, J=6.9 Hz), 5.08–5.21 (m, 4H), 6.22 (d, 1H, J=6.9 Hz), 6.92–7.55 (m, 16H), 8.05–8.09 (m, 2H)

Example 21

Production of Oxazoline [IV]

To a mixture of benzyl (2S)-2-benzoylamino-3-(3,4-dibenzyloxyphenyl)propanoate (2.29 g, 4.00 mmol), copper acetate monohydrate (8 mg, 0.04 mmol) and acetone (30 g), a solution of ammonium cerium (IV) nitrate (5.92 g, 10.8 mmol) and water (25 g) was added over 0.5 hours, and then the mixture was stirred at the same temperature (60° C.) for 8 hours.

After hydroquinone (0.18 g) and an aqueous 10% sodium hydroxide solution (4.3 g) were added, the low-boiling point component was distilled off to obtain a slurry. Ethyl acetate (50 ml) was added to the slurry, 10%-hydrochloric acid was added to dissolve an inorganic salt, followed by partitioning to obtain a partitioned organic layer. The partitioned organic layer was washed and treated with a saturated saline solution, dried over anhydrous sodium sulfate and concentrated under reduced pressure. The residue was treated with silica gel chromatography and 1.71 g (3.00 mmol, yield: 75%) of benzyl (4S, 5R)-5-(3,4-dibenzyloxyphenyl)-2-phenyl-2-oxazoline-4-carboxylate was obtained.

FD-MS: 569

$^1$H-NMR (δ): 4.75 (d, 1H, J=6.9 Hz), 5.05–5.31 (m, 6H), 6.23 (d, 1H, J=6.9 Hz), 6.83–7.52 (m, 21H), 8.03–8.10 (m, 2H)

Example 22

Production of Oxazoline [IV]

The procedure of Example 21 was repeated, except that methyl (2S)-2-benzoylamino-3-(3,4-dimethoxyphenyl)propanoate (1.68 g, 4.89 mmol) was used instead of benzyl (2S)-2-benzoylamino-3-(3,4-dibenzyloxyphenyl)propanoate, and 0.97 g (2.8 mmol, yield: 58%) of methyl (4S,5R)-5-(3,4-dimethoxyphenyl)-2-phenyl-2-oxazoline-4-carboxylate was obtained.

$^1$H-NMR (δ): 3.85 (s, 3H), 3.87 (s, 3H), 3.88 (s, 3H), 4.84 (d, 1H, J=7.6 Hz), 5.84(d, 1H, J=7.6 Hz), 6.81–7.06 (m, 3H), 7.41–7.54 (m, 3H), 8.04–8.08 (m, 2H)

Example 23

Production of Oxazoline [IV]

The procedure of Example 21 was repeated, except that methyl (2S)-2-benzoylamino-3-(2-chloro-4,5-dimethoxyphenyl)propanoate (1.85 g, 4.90 mmol) was used instead of benzyl (2S)-2-benzoylamino-3-(3,4-dibenzyloxyphenyl)propanoate, and 1.46 g (3.89 mmol, yield: 79%) of methyl (4S, 5R)-5-(2-chloro-4,5-dimethoxyphenyl)4-carboxylate was obtained.

$^1$H-NMR (67): 3.79 (s, 3H), 3.85 (s, 3H), 3.88 (s, 3H), 4.78 (d, 1H, J=6.9 Hz), 6.2 2 (d, 1H, J=6.9 Hz), 6.83 (s, 1H), 6.90 (s, 1H), 7.42–7.58 (m, 3H), 8.05–8.09 (m, 2H)

Examples 24

Production of Threo DOPS [III] from Oxazoline [IV]

(1) The oxazoline ring was opened and the protecting group $R^3$ was eliminated.

Methyl (4S,5R)-5-(3,4-dibenzyloxyphenyl)-2-phenyl-2-oxazoline-4-carboxylate (987 mg, 2.00 mmol) was added to 1N-hydrochloric acid (20 ml) with stirring, and the mixture was refluxed for 17 hours. After cooling to room temperature, the reaction mixture was neutralized with 1N-sodium hydroxide to obtain a precipitated crystal. The precipitated crystal was filtered to obtain 637 mg (1.63 mmol, yield: 81%) of L-threo-3-(3, 4-dibenzyloxyphenyl) serine.

(2) Removing the $R^1$ and $R^2$ protecting groups

A mixture of L-threo-3-(3,4-dibenzyloxyphenyl)serine (597 mg, 1.52 mmol), 5%-palladium-carbon (10 mg), isopropanol (5 g) and aqueous 5%-aqueous acetic acid was reduced with hydrogen at room temperature under atmospheric pressure for 15 hours. The reaction mixture was then adjusted to pH 1 with 1N-hydrochloric acid and filtered to obtain filtrate. The filtrate was concentrated under reduced pressure and neutralized with 1N-sodium hydroxide. The precipitated crystal was then filtered to obtain 291 mg (1.36 mmol, yield: 91%) of L-threo DOPS.

Melting point of L-threo DOPS: 223° C.

Optical rotation: $[\alpha]^{20}_D$–37.2(C=1, 1N-hydrochloric acid)

Example 25

Production of Threo DOPS [III] from Oxazoline [IV]

(1) Removing the $R^1$ and $R^2$ protecting groups.

A mixture of methyl (4S,5R)-5-(3,4-dibenzyloxyphenyl)-2-phenyl-2-oxazoline-4-carboxylate (494 mg, 1.00 mmol), 5%-palladium-carbon (64 mg) and isopropanol (5 g) was reduced with hydrogen at room temperature under atmospheric pressure for 15 hours. The reaction mixture was filtered and then the filtrate was concentrated under reduced pressure. The residue was treated with silica gel chromatography to obtain 263 mg (0.84 mmol, yield: 84%) of methyl (4S,5R)-5-(3, 4-dihydroxyphenyl)-2-phenyl-2-oxazoline-4-carboxylate.

(2) Opening the oxazoline ring and removing the $R^3$ protecting group.

Methyl (4S,5R)-5-(3,4-dibenzyloxyphenyl)-2-phenyl-2-oxazoline-4-carboxylate (157 mg, 0.50 mmol), was added to 1N-hydrochloric acid (5 ml) with stirring, and the mixture was refluxed for 17 hours. After cooling to room temperature, the reaction mixture was washed with ether and neutralized with 1N sodium hydroxide to obtain precipitated crystals. The precipitated crystal then was filtered to obtain 76 mg (0.36 mmol, yield: 71%) of L-threo DOPS.

Examples 26

Production of Threo DOPS [III] from Oxazoline [IV]

Methyl (4S,5R)-5-[3, 4-(dimethylmethylenedioxy)phenyl]-2-phenyl-2-oxazoline-4-carboxylate (500 mg, 1.41 mmol) was added to 2N-hydrochloric acid (10 ml) with stirring at room temperature, and the mixture was then refluxed for 16 hours. After cooling to room temperature, about 25° C., the reaction mixture was concentrated under reduced pressure and neutralized with an aqueous 1N-sodium hydroxide solution to obtain a precipitated crystal. The precipitated crystal then was filtered to obtain 265 mg (1.24 mmol, yield: 88%) of L-threo DOPS.

What is claimed is:

1. A process for producing racemic or optically active oxazolines represented by the formula [IV]:

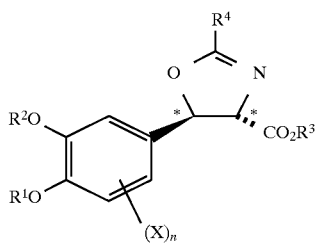

which comprises
reacting a racemic or optically active N-acyl-3,4-dihydroxyphenylalanine derivative represented by the formula [I]:

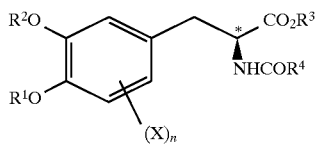

wherein $R^1$ and $R^2$ independently represent a protecting group for a
hydroxyl group;

$R^3$ is a protecting group for a carboxyl group;

$R^4$ is an optionally substituted alkyl group or an optionally substituted phenyl group;

X is a halogen atom;

n is 0, 1, 2 or 3; and each carbon marked with the symbol * is an asymmetric carbon, with a halogen radical generator, a cerium (IV) salt in the presence or absence of a copper catalyst, or a persulfate salt in the presence of a copper catalyst.

2. Racemic or optically active oxazolines represented by the formula [IV]:

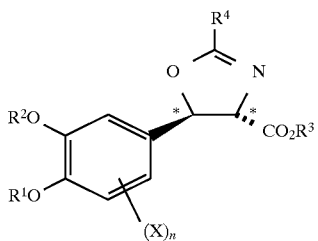

wherein $R^1$ and $R^2$ independently represent a protecting group for a hydroxyl group;

$R^3$ is a protecting group for a carboxyl group;

$R^4$ is an optionally substituted alkyl group or an optionally substituted phenyl group which may have a substituent;

X is a halogen atom;

n is 0, 1, 2 or 3; and each carbon marked with the symbol * is an asymmetric carbon.

* * * * *